United States Patent [19]

Francia

[11] Patent Number: 4,578,460

[45] Date of Patent: Mar. 25, 1986

[54] N-6-AMINOPURINYL-4-HYDROXY-2-METHYL-2H-1,2-BENXOTHIAZINE-3-CARBOXAMIDE 1,1-DIOXIDE COMPOUND

[75] Inventor: Giorgio A. Francia, Milan, Italy

[73] Assignee: Francia Farmaceutici s.r.l., Italy

[21] Appl. No.: 539,073

[22] Filed: Oct. 4, 1983

[30] Foreign Application Priority Data

Oct. 22, 1982 [IT] Italy .................. 23888 A/82

[51] Int. Cl.[4] .......................................... C07D 279/02
[52] U.S. Cl. ...................................................... 544/49
[58] Field of Search .................... 544/49; 424/246; 514/225

[56] References Cited

U.S. PATENT DOCUMENTS

| Re. 29,836 | 11/1978 | Zinnes et al. | 544/49 |
| 3,591,584 | 7/1971 | Lombardino | 544/49 |
| 4,289,879 | 9/1981 | Lombardino | 544/49 |
| 4,434,163 | 2/1984 | Lombardino | 544/49 |

FOREIGN PATENT DOCUMENTS 0070888  5/1982  Japan ........................ 544/49

OTHER PUBLICATIONS

Ito, Shinichi, C.A., vol. 97, 1982, p. 729, (127648a).
Goodman et al., "The Pharmacological Basis of Therapeutics", 6th ed., Macmillan Publ. Co., N.Y., N.Y., 1975, pp. 717, and 720–723.

*Primary Examiner*—Henry R. Jiles
*Assistant Examiner*—J. G. Mullins
*Attorney, Agent, or Firm*—Ostrolenk, Faber, Gerb & Soffen

[57] ABSTRACT

The invention relates to a derivative of 4-hydroxy-2-methyl-2H-1,2-benzothiazine-3-carboxamide 1,1-dioxide of the formula:

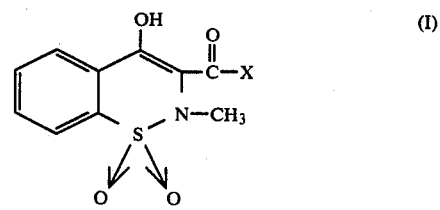

in which X is 6-aminopurinyl. The above compound exhibits anti-inflammatory activity.

1 Claim, No Drawings

N-6-AMINOPURINYL-4-HYDROXY-2-METHYL-2H-1,2-BENXOTHIAZINE-3-CARBOXAMIDE 1,1-DIOXIDE COMPOUND

DESCRIPTION OF THE INVENTION

The present invention relates to compounds having pharmacological activity.

More precisely, this invention relates to compounds useful in human as well as veterinary therapy for the treatment of various types of inflammatory conditions.

Further, the present invention concerns a process for the preparation of said derivatives.

From U.S. Pat. No. 3,591,584, several benzothiazine dioxides are known. Such compounds have an anti-inflammatory activity and, as they are not steroidal compounds, they are free from the undesired inherent side effects of the steroidal anti-inflammatory compounds.

The derivatives of this invention correspond to the following formula:

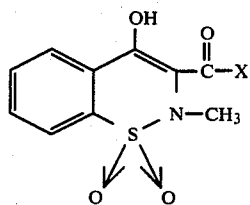

in which X represents the radical of one of the following compounds: 6-aminopurine, amino-imidazole, amino-oxasole; or of an amino-acid such as glutamic acid, aspartic acid, histidine, lysine and the like.

The compounds of this invention have very good anti-inflammatory properties and are, therefore, useful in the therapy for the treatment of inflammatory states of various origins.

Particularly, the compounds of the present invention are quite suitable for the treatment of rheumatic diseases comprising rheumatoid arthritis, due also to their ability to reduce the swelling which usually accompanies such diseases.

Of all the compounds of this invention, the one now preferred can be represented by the following formula:

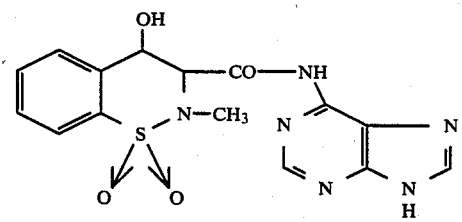

which can be named N-(6-amminopurinyl)-4-hydroxy-2-methyl-2H-1,2-benzothiazine-3-carboxamide 1,1-dioxide.

The synthesis of compound (V) can be so outlined: treating of sodium saccharinate (I) with methyl chloroacetate produces the methyl ester of 3-oxo-1,2-benzoisothiazoline-2-acetic acid (II), the rearrangement of which in a basic medium provides the methyl ester of 6-oxy-2H-1,2-benzothiazine-3-carboxylic acid (III), from which, by methylating with CH₃ I, compound (IV) is obtained.

Reaction of (IV) with adenine (6-aminopurine) under drastic conditions at a temperature higher than 150° provides (V) with a 20% yield.

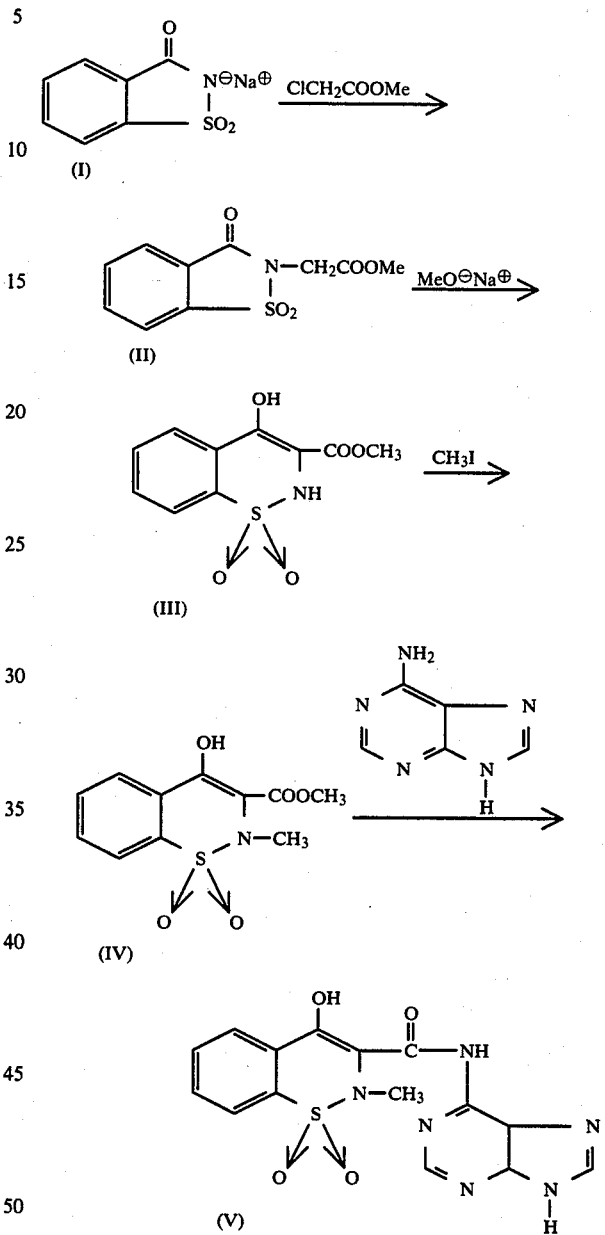

The following example aims at better illustrating this invention.

EXAMPLE 1

A solution of 4.0 g (0.015 mole) of methyl-4-oxy-2-methyl-2H-1,2 bezothiazine-3-carboxylate 1,1-dioxide and 2.23 g (0.0165 moles) of adenine in 300 ml of anhydrous xylene is refluxed 24 hours in a Soxhlet and in the presence of molecular sieves.

From time to time, a part of the solvent is distilled off and replaced by acid xylene.

The reaction progress is maintained by t.l.c. (CHCl₃/MeOH 4:1).

After cooling and filtering the suspension, 1.1. g. of compound (V) by repeated crystallizations from MeOH, is obtained.

Yield ~20%.
FeCl₃ assay for positive (red) enolic OH.
Empirical formula $C_{15}H_{12}N_6SO_4$.
Molecular weight: 373.06.
Melting point: 206°–°.
Analysis: C=48.32; H=3.32; N=22.57; S=8.63; O=17.16.

The product is in the powder form, light yellow in color, nearly odourless, and tasteless. It is practically insoluble in H₂O, little and soluble in ether and chloroform, soluble in methanol and ethanol, particularly when hot.

Mass spectrum: it was obtained on a Varian Mat CH5 spectrometer by direct introduction at 70 eV.

¹H NMR Spectrum: it was obtained by Varian T 60. Solvent: DMSO d₆ (I 1.02–2.31;7.10).

IR Spectrum: it was performed by a Perkin Elmer spectrofotometer, Mod. 180: 6.0; 6.20; 6.26μ (endo form).

Thin layer chromatography: performed on silica gel G plates; (0.25 mm layer); Eluent: CHCl₃/MeOH 4:1; Rf: 0.5 (average).

I claim:

1. A derivative of 4-hydroxy-2-methyl-2H-1,2-benzothiazine-3-carboxamide 1,1-dioxide of the formula:

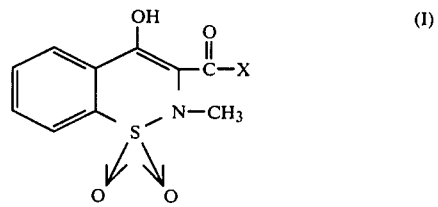

in which X represents a radical of 6-aminopurine, amino-imidazole, glutamic acid, aspartic acid, histidine, or lysine.

* * * * *